(12) United States Patent
Goldman et al.

(10) Patent No.: US 9,855,408 B2
(45) Date of Patent: Jan. 2, 2018

(54) KINK-RESISTANT GUIDEWIRE WITH IMPROVED RIGIDITY

(71) Applicant: C. R. Bard, Inc., Murray Hill, NJ (US)

(72) Inventors: David Goldman, Decatur, GA (US); Michael Dolgin, Cincinnati, OH (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 15/302,157

(22) PCT Filed: Apr. 29, 2015

(86) PCT No.: PCT/US2015/028366
§ 371 (c)(1),
(2) Date: Oct. 5, 2016

(87) PCT Pub. No.: WO2015/168335
PCT Pub. Date: Nov. 5, 2015

(65) Prior Publication Data
US 2017/0028173 A1    Feb. 2, 2017

Related U.S. Application Data

(60) Provisional application No. 61/985,887, filed on Apr. 29, 2014.

(51) Int. Cl.
*A61B 5/00*    (2006.01)
*A61M 25/09*    (2006.01)

(52) U.S. Cl.
CPC ... *A61M 25/09* (2013.01); *A61M 2025/09075* (2013.01); *A61M 2025/09108* (2013.01);
(Continued)

(58) Field of Classification Search
CPC ........ A61M 25/09; A61M 2025/09083; A61M 2025/09091; A61M 2025/09116; A61M 2025/09191
(Continued)

(56) References Cited

U.S. PATENT DOCUMENTS 4,925,445 A   5/1990   Sakamoto et al.
4,991,602 A   2/1991   Amplatz et al.
(Continued)

FOREIGN PATENT DOCUMENTS

EP   1491230 A2   12/2004
WO   98/16274 A1   4/1998
WO   2015/168335 A1   11/2015

OTHER PUBLICATIONS

PCT/US2015/028366 filed Apr. 29, 2015 International Search Report dated Aug. 5, 2015.
(Continued)

*Primary Examiner* — Max Hindenburg
(74) *Attorney, Agent, or Firm* — Rutan & Tucker, LLP (57) ABSTRACT

A guidewire, methods of manufacture, and methods of use is described. The guidewire may include a core having one or more preformed ribs along a portion thereof. The ribs may form a portion of the outer surface of the guidewire or form a texture or shape of the outer surface of the guidewire. The ribs and outer texture of the guidewire can beneficially help the guidewire remain in a desired location in a body and help prevent or limit migration. Forming the ribs on the outer surface of the core may enable the guidewire to have greater rigidity and stiffness. The core may include a reduced diameter region distal of the ribs. The guidewire may include a cap over the reduced diameter region of the core.

6 Claims, 4 Drawing Sheets

(52) U.S. Cl.
CPC .............. *A61M 2025/09116* (2013.01); *A61M 2025/09175* (2013.01); *A61M 2025/09191* (2013.01); *A61M 2210/1078* (2013.01); *A61M 2210/1085* (2013.01); *A61M 2210/1089* (2013.01)

(58) Field of Classification Search
USPC ........................................................ 600/585
See application file for complete search history.

(56) References Cited

U.S. PATENT DOCUMENTS

| | | | |
|---|---|---|---|
| 6,113,557 A | 9/2000 | Fagan et al. | |
| 6,142,958 A | 11/2000 | Hammarstrom et al. | |
| 6,390,992 B1 | 5/2002 | Morris et al. | |
| 6,926,725 B2 | 8/2005 | Cooke et al. | |
| 7,097,620 B2 | 8/2006 | Corl et al. | |
| 7,169,118 B2 | 1/2007 | Reynolds et al. | |
| 8,574,171 B2 | 11/2013 | Nesbitt et al. | |
| 9,259,555 B2 * | 2/2016 | Nabeshima | A61M 25/09 |
| 2004/0142643 A1 | 7/2004 | Miller et al. | |
| 2004/0167439 A1 | 8/2004 | Sharrow | |
| 2004/0215109 A1 | 10/2004 | Pingleton et al. | |
| 2007/0049847 A1 | 3/2007 | Osborne | |
| 2013/0231752 A1 | 9/2013 | Rosenbaum et al. | |

OTHER PUBLICATIONS

EP 15786448.9 filed Oct. 12, 2016 Extended European Search Report dated Mar. 16, 2017.

* cited by examiner

KINK-RESISTANT GUIDEWIRE WITH IMPROVED RIGIDITY

PRIORITY

This application is a U.S. national stage application under 35 USC §371 of International Application No. PCT/US15/28366, filed Apr. 29, 2015, which claims the benefit of priority to U.S. Provisional Application No. 61/985,887, filed Apr. 29, 2014, which is incorporated by reference in its entirety into this application.

BACKGROUND

This application discusses guides or guidewires for use in medical procedures, including flexible, kink-resistant guides or guidewires.

Elongated, flexible guidewires can be used in medical procedures to gain access to specific internal sites within the body without major surgery. Guidewires can be advanced through the body, for example, through peripheral blood vessels, the gastrointestinal tract, or the urinary tract. Guidewires can be used in, among other fields, cardiology, electrophysiology, gastroenterology, urology, and radiology.

Once positioned indwelling, the guidewire defines the path for the introduction of catheters and/or other medical instruments to a desired site; however, such instruments may be less wieldy than the guidewire, have significantly more mass, and create a risk of kinking the guidewires as they are advanced over the guidewire.

Also, hydrophilic or lubricious guidewires can be difficult to use because they may too easily migrate or slip from the desired location in a patient's body. Further, a clinician wearing plastic or latex gloves may not be able to properly grip and manipulate a hydrophilic or lubricious guidewire.

A guidewire may be constructed with a central core or core wire and a coil along the distal portion of the guidewire or surrounding the core. Generally, the dimension or size of the core essentially defines the stiffness of the guidewire along its length. For a given core material, the greater its cross-section, the greater the stiffness of the overall guidewire. The choice of core wire material affects the performance characteristics of the guidewire and affects its cost. Further, using an outer coil requires the diameter of the core wire inside the coil to be reduced or smaller to fit inside the coil and produce a guidewire with an overall outer diameter that is not too large. Stainless steel core guidewires may be inexpensive but, with reduced or small diameters, can be prone to kinking during advancement of catheters and/or other instruments thereover. Cores made of fiberglass composites may be more resistant to kinking but they can be more prone to abruptly snapping, and it is difficult to provide a taper to the distal end of the fiberglass core, to increase flexibility of the distal end, without splintering. If a guidewire is not sufficiently stiff or rigid, it may be more prone to kinking and may be more difficult to navigate and direct to a desired location in a body.

There is a need for a guidewire that maintains a relatively high degree of stiffness for better maneuverability and has beneficial outer frictional or texture characteristics.

SUMMARY

Embodiments of, and enhancements for devices, components, assemblies, systems, methods, etc. for use in medical treatment, including medical procedures using a guidewire, are described herein.

A guidewire (the term "guidewire" is used to refer to guides, guidewires, and similar devices) may include a proximal end, a distal end, and a core. A portion of the guidewire, e.g., the core, may include one or more preformed ribs along all or a portion thereof, e.g., a proximal portion. A portion of the guidewire, e.g., the core, may include a reduced diameter region or end. For example, a distal region of the guidewire may be tapered or otherwise have a reduced diameter. The reduced diameter region of the guidewire may include a cap or sleeve thereon. The cap or sleeve may be shaped/configured to fit over the reduced diameter region so as to create an outer diameter that is the same as or similar to (e.g., ±0.1 inches) the outer diameter of a full diameter region of the guidewire or the region of the guidewire having preformed ribs extending therethrough. The core may include an outer polymeric coating over a portion or an entirety thereof, including over preformed ribs.

In one embodiment, a guidewire includes a core. The core may include ribs formed along a first portion of the core, the first portion of the core having a first diameter, wherein the ribs increase the friction of the outer surface of the guidewire. The ribs may be arranged in the shape of one or more helical coils along the first portion. Other shapes/configurations may also be used as described elsewhere herein. The core may also include a reduced diameter region distal of the first portion having a second diameter less than the first diameter. The guidewire may also include a cap having the same or a similar diameter to the first diameter, the cap positioned over the reduced diameter region of the core such that an edge of the cap abuts the first portion. The cap may have a smooth, uniform outer surface. The reduced diameter region of the core may include a channel adjacent to the first portion of the core, wherein the channel may be shaped to mate with a portion of the cap in a snap-fit or threaded connection. The guidewire may include a coating on the first portion of the core. The coating may extend over the cap and form a smooth, unbroken outer surface transition between the first portion of the core and the cap.

A method of medical treatment or using a guidewire may include obtaining a guidewire, wherein the guidewire includes a core having ribs formed along an outer surface of a first portion of the core having a first diameter, wherein the ribs increase the surface friction of the guidewire. The method may include inserting a distal end of the guidewire into a vessel of a patient's body. The method may also include navigating the guidewire to a desired location in the patient's body. Navigating the guidewire to a desired location may include navigating the guidewire through a urethra and bladder and into a ureter of the patient's body. The guidewire may be navigated to, or near to, a kidney of a patient. The ribs may help hold the guidewire in the desired location in the patient's body to reduce the risk of the guidewire migrating from the desired location. Obtaining a guidewire may further comprise obtaining a guidewire wherein the core further includes a reduced diameter region distal of the first portion having a second diameter less than the first diameter. Obtaining a guidewire may also comprise obtaining a guidewire having a cap with the same or a similar diameter to the first diameter, the cap positioned over the reduced diameter region of the core such that an edge of the cap abuts the first portion.

A method of manufacturing a guidewire may include obtaining an elongate guidewire core material (e.g., may be similar to the initial material described elsewhere herein as being formed into the core) having a first end and a second end and forming one or more ribs on a surface of the elongate guidewire core material, wherein the ribs form a pattern visible on an outer surface of the guidewire. Forming one or more ribs may be accomplished by twisting the second end around a longitudinal axis of the elongate guidewire core material while the first end remains stationary or is twisted in an opposite direction. Such an action may plastically deform the elongate guidewire core material to have ribs thereon. The plastic deformation may set naturally or may be treated (e.g., heat treated) to set the deformation and/or ribs into the material. Optionally, forming one or more ribs may be accomplished by machining/grinding the ribs into the surface of the elongate guidewire core material. The elongate guidewire core material may be formed into a core similar to those described elsewhere herein. The method may further include forming a reduced diameter region in the elongate guidewire core material. The method may further include attaching a cap over the reduced diameter region such that an edge of the cap abuts at least one of the one or more ribs or a region of the core including the one or more ribs.

BRIEF DESCRIPTION OF THE DRAWINGS

The disclosed devices, components, assemblies, systems and methods can be better understood with reference to the description taken in conjunction with the following drawings, in which like reference numerals identify like elements. The components in the drawings are not necessarily to scale.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Described herein are devices, components, assemblies, systems, methods, etc. for medical treatment, including medical treatment using a guidewire. The description and accompanying figures, which describe and show certain embodiments, are made to demonstrate, in a non-limiting manner, several possible configurations of guides, guidewires, devices, components, assemblies, systems, etc. and various methods of using them according to various aspects and features of the present disclosure. Accordingly, the disclosure is not limited to the specific embodiments described. Rather, the inventive principles associated with the embodiments described herein, including with respect to the guides, guidewires, components, assemblies, systems, methods, etc. described herein, may be applied in a variety of ways, including to other types of devices, components, assemblies, systems, methods, etc. General principles and features are described herein sufficiently to enable one to develop a variety of implementations/applications without undue experimentation.

This document does not intend to distinguish between components that differ in name but not function. In the following discussion and in the claims, the terms "including," "includes," "comprising," "have," and "has" are used in an open-ended fashion, and thus should be interpreted to mean "including, but not limited to." The word "or" is used in the inclusive sense (i.e., "and/or") unless a specific use to the contrary is explicitly stated. The terms "guidewire" and "guidewires" are used to refer to guidewires and more broadly to guides and similar devices, unless expressly stated otherwise. As used herein, "proximal" refers to a direction or region that is relatively closer to a clinician during operation, and "distal" refers to a direction or region that is relatively further away from the clinician during operation.

Figure 1:
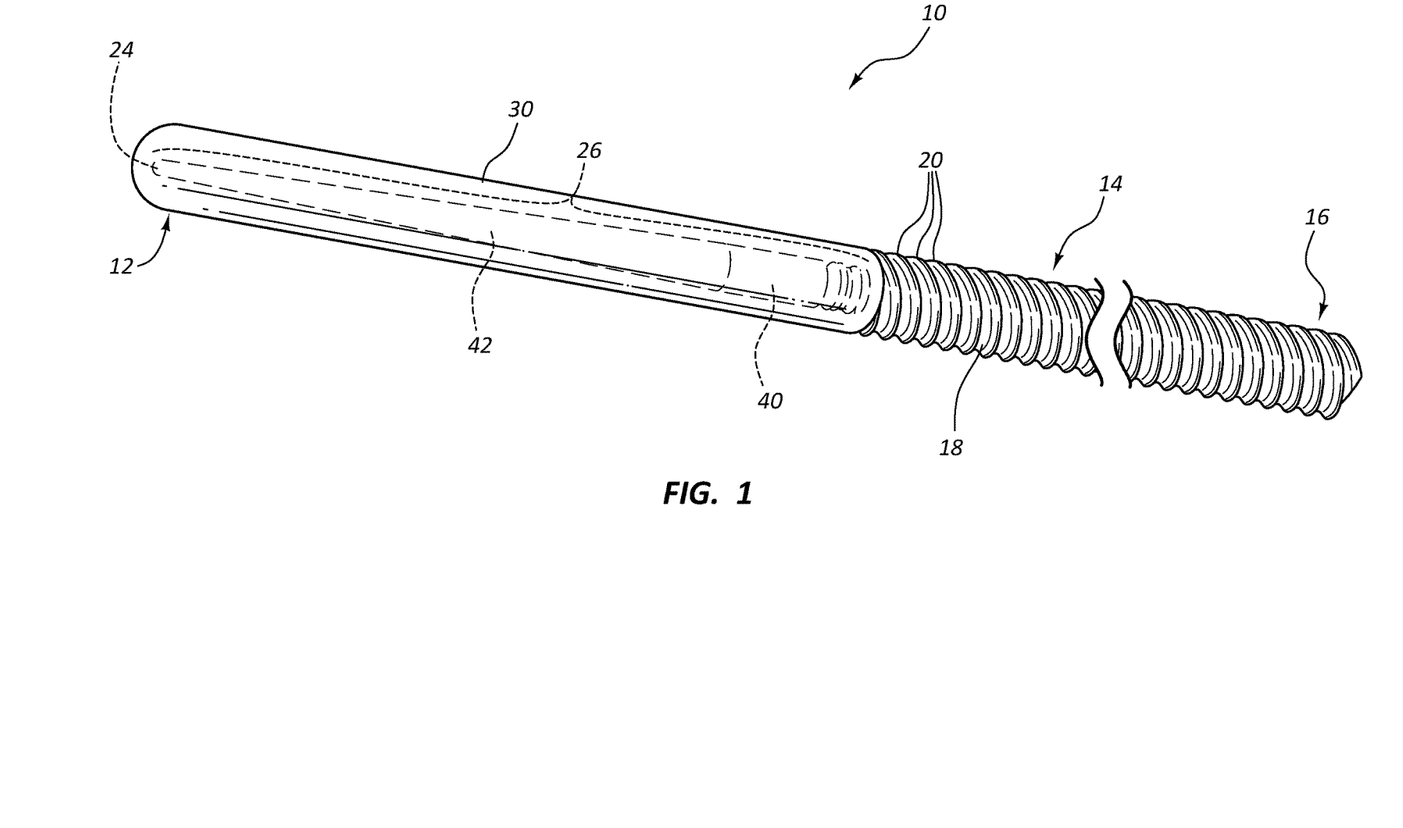
FIG. 1 is a perspective view of an exemplary embodiment of a guidewire having a core and a cap.

FIG. 1 illustrates an exemplary guide or guidewire 10, which can be used in medical procedures. In one embodiment, the guidewire 10 may be used to introduce other devices along the guidewire 10 to a target location inside a patient, e.g., the guidewire 10 may be used to guide another device into a patient's vessels, such as a patient's urinary tract, vasculature, and/or other vessels. As seen in FIG. 1, the guidewire 10 has a proximal end 16, a distal end 12, and an intermediate region 14 spanning the distance between the proximal end 16 and the distal end 12. The guidewire 10 may be formed using a core 18. The guidewire 10 may also include a cap 30, and/or a coating 50. While the core 18 may be covered in part by cap 30 and/or be covered in whole or in part by a coating 50, portions of the core 18 may remain uncovered. It is also possible to make guidewire 10 consisting entirely of the core 18.

Figure 2:
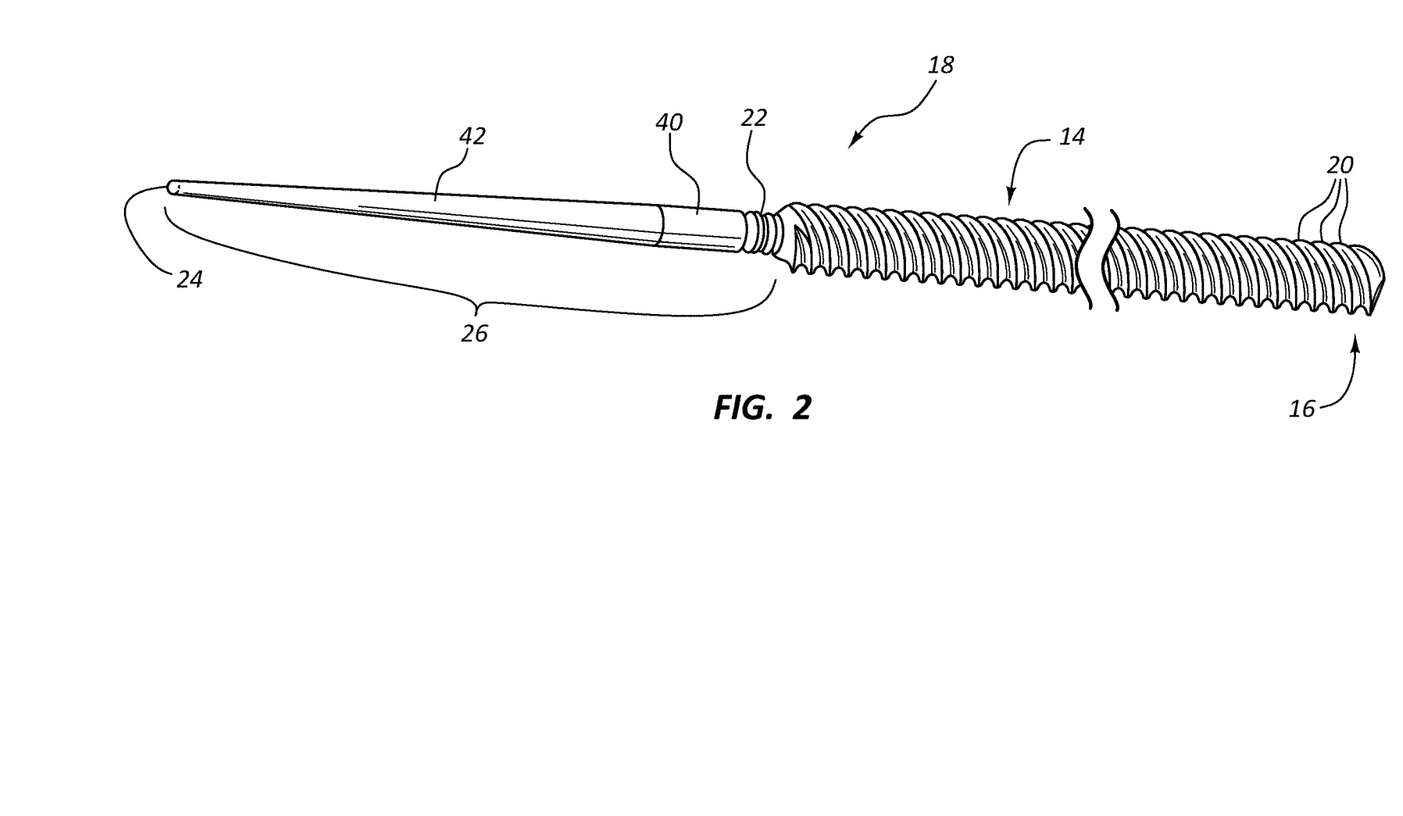
FIG. 2 is a perspective view of an exemplary embodiment of a core that may be used in a guidewire as shown in FIG. 1.

FIG. 2 illustrates an exemplary core 18 that may be used to form the guidewire 10. A guidewire may be constructed with a central core, which can be made of stainless steel, other metal, and/or another material to provide stiffness to the guidewire, and may have a distal or forward end portion of increased flexibility to better enable the clinician to maneuver the guidewire into the appropriate passageway. The portion of the guidewire proximal the flexible distal end portion can provide the requisite stiffness to support and to guide the medical instrument to the site accessed by the guidewire. Generally, the core of a guidewire will determine the overall rigidity or stiffness of the guidewire. Greater rigidity or stiffness in the guidewire proximal of the distal end beneficially increases the maneuverability, strength, and durability of the guidewire. A coil (e.g., a spring coil) may be positioned over all or a portion of the core (e.g., the core may pass longitudinally through a center of the coil). The core wire may be moveable within the coil to permit the clinician to selectively adjust the flexibility of the guidewire as the guidewire is being positioned and while a catheter or other instrument is being advanced thereover. In designs that include a coil, a weld can be made at the distal end of the coil to provide an atraumatic tip, and a safety wire welded to the tip can extend proximally, within the coil, to better ensure that the tip does not separate from the guidewire during use. However, if a separate coil is used over the core, the diameter of the core within the coil must be reduced or less than the overall outer diameter desired for the guidewire in order to maintain a reasonable overall diameter thereof. Because the core has the largest impact on the rigidity or stiffness of the guidewire, reducing the diameter of the core or having a core diameter less than the overall guidewire diameter limits the rigidity or stiffness possible for the overall guidewire.

Rather than wrapping the core of a guidewire with a spring coil wire that adds no rigidity to the guidewire shaft, in one embodiment preformed ribs may be formed around a core or on an outer surface of the core itself. This allows the core to be thicker or have a greater diameter thereby resulting in increased rigidity or stiffness of the guidewire and greater kink-resistant properties. A guidewire formed with ribs on the core may be, for example, 2.5 to 3 times more rigid than a guidewire having the same outer diameter formed with a core inside of a spring coil. The increased rigidity or stiffness may beneficially allow a clinician or doctor more control and maneuverability of the guidewire when manipulated from a proximal portion of the wire, e.g., adjustments/manipulations made at the proximal end of the guidewire can better translate to the distal portion of the guidewire, e.g., twisting/rotation at a proximal region/end may be better transferred to the distal end.

Further, the increased rigidity or stiffness may help prevent buckling or undesired over bending of the guidewire. For example, in a medical procedure where the guidewire must be advanced through the urethra of a patient, into the bladder, and then into the ureter (and possibly to a kidney), the added stiffness or rigidity can help maneuver the guidewire along the path without complications that would be experienced by a more flexible guidewire, e.g., a stiffer guidewire may be able to better move into the ureter from the bladder than a more flexible guidewire that might buckle or bend too much in the bladder. The preformed ribs may provide beneficial surface characteristics to the guidewire 10. For example, the preformed ribs may increase outer surface friction of the guidewire 10, which can help the guidewire to remain better in a desired location in the body without drifting or slipping from that location. Further, additional friction on the outer surface of the guidewire may help the clinician or doctor to better grip, twist/rotate, and otherwise maneuver the guidewire from a proximal region. A clinician or doctor will likely be wearing plastic or latex gloves during the procedure, and the gloves can slip over a guidewire too easily without enough surface friction on the guidewire. Methods for creating the preformed ribs are described in more detail below.

FIG. 2 shows an exemplary embodiment with ribs 20 along a portion of the core 18. As shown in FIG. 2, the core 18 may also include a reduced diameter region 26 (some or all of which may be tapered) ending in a distal tip 24. The reduced diameter region 26 may also include a channel 22 for better connection to a cap 30. The distal tip 24 may be blunt or atraumatic to help avoid injury. In addition to or instead of ribs 30, other types of texturing, grooving, etching, and patterns may be added to the outer surface of the core 18 and/or guidewire 10 to achieve a desired surface friction.

The ribs 20 may extend along the full length of the core 18 or may extend along only a portion of the core 18 (e.g., ribs 20 may extend only along a proximal region of the core wire 18 or may extend over all the core wire 18 except for the reduced diameter region 26). The ribs 20 may be formed by one ridge circling or coiling/spiraling along a length of the core 18, or may be any number of ridges or ribs (e.g., 2, 3, 4, 5, 6, 7, or 8 ridges coiling/spiraling along a length of the core, or more ridges or ribs at different points along the core 18, e.g., 2-100 ribs or 20-70 ribs). The ribs 20 may be formed in a variety of shapes and configurations. For example, the ribs 20 may be curved (e.g., forming a rounded cross-sectional shape, or forming a semi-circular cross-sectional shape) or include one or more edges and/or angles (e.g., formed with a triangular, square, pentagonal, hexagonal, or other polygonal shaped cross-section). If formed with one or more edges and/or angles, the edges and/or angles may have rounded edges or angles, e.g., forming a combination of a curved and edged cross-section. The ribs 20 may be uniform in shape or may vary in shape along their length or path. The ribs 20 may be arranged in a variety of configurations as well. For example, the ribs 20 may be arranged in a helical shape along the core 18 and guidewire 10. The helical shape can wind either clockwise or counterclockwise looking down the length of the core 18. Optionally, the ribs 20 may be formed as a plurality of circlets or a series of parallel ribs lined up adjacent to each other along the length of the core 18 and guidewire 10, e.g., each rib may form a circle around the longitudinal axis of the core 18 on the outer surface of the core. Other configurations are also possible, e.g., a combination of helical and non-helical or circular shapes, a sinusoidal shape along the length and/or curvature of the core 18, etc. The ribs 20 may be shaped and arranged to provide optimal surface characteristics to the guidewire, e.g., optimal frictional characteristics (see discussion of outer surface frictional characteristics above).

The ribs 20 of the core 18 can be formed in a variety of ways, including machining and/or grinding a core 18 or material used to form core 18 (e.g., guidewire core material) to the desired shape/configuration, twisting/rotating a portion of the core 18 or material used to form core 18, a mold, injection molding, laser cutting and/or etching, other cutting and/or etching, 3D printing, etc. With such a unibody construction, the chances of manufacturing failures are minimized, as are manufacturing costs. The ribs 20 can aid the clinician in manipulation of the guidewire and help maintain the guidewire in position within the patient, which is advantageous for both the clinician and the patient. Further, forming the ribs 20 on an outer surface of a core rather than merely having a spring coil over a smaller internal core provides several advantages, reduced cost (e.g., a separate spring coil is not required), makes manufacture easier (fewer parts to keep track of and connect), and makes the guidewire more reliable (fewer parts means fewer opportunities for failures and defects.)

FIG. 2 shows an embodiment in which the ribs 20 were formed on the core 18 or material used to form core 18 by machining using a centerless grinding process. A centerless grinding process can be used to provide ribs along the outer body of the core 18 or material used to form core 18 in a variety of shapes and configurations (see shapes and configurations discussed above). Centerless grinding is a process that grinds the surface of a guidewire core material (e.g., a bar or wire). Forming ribs right on the outer surface of the core 18 allows the guidewire 10 to have a thicker core (e.g., as compared to a core inside of a separate spring coil) and be formed with optimal levels of stiffness and flexibility throughout the guidewire's length. Some flexibility can be added to the core 18 by machining more of the outer surface, e.g., to narrow the diameter of the core and/or provide grooves or channels of reduced diameter between the ribs that allow more flexibility along the length of the core). In any case, this method makes it easier to optimize the desired rigidity or stiffness of the core 18 and the guidewire 10. Further, more rigidity and stiffness is possible with this type of core 18 and guidewire 10 than would be possible with a guidewire of the same outer diameter formed of a narrow core wire encircled by a separate spring coil.

In centerless grinding, the core 18 or material used to form the core 18 (e.g., guidewire core material) may be held between two grinding wheels, rotating in the same direction at different speeds, and a holding platform. A grinding wheel is on a fixed axis and rotates such that the force applied to the guidewire 10 is directed downward, against the holding platform. This wheel performs the grinding action by having a higher speed than the guidewire 10 at the point of contact. The other wheel, known as the regulating wheel, is movable. This wheel is positioned to apply lateral pressure to the guidewire 10, and may have either a very rough or rubber-bonded abrasive to trap the guidewire 10. The speed of the two wheels relative to each other provides the grinding action and determines the rate at which material is removed from the guidewire 10. During operation the guidewire 10 turns with the regulating wheel, with the same linear velocity at the point of contact and no slipping. The grinding wheel turns faster, slipping past the surface of the guidewire 10 at the point of contact and removing chips of material as it passes.

Figure 3A:
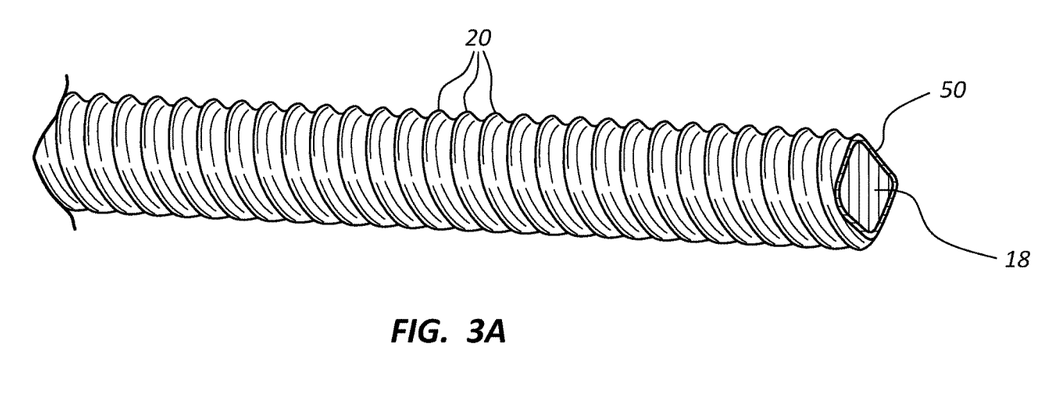
FIG. 3A is a close-up view of an exemplary section of a core in which ribs have been formed by rotating/twisting one portion of the core or core material relative to another portion thereof.
Figure 3B:
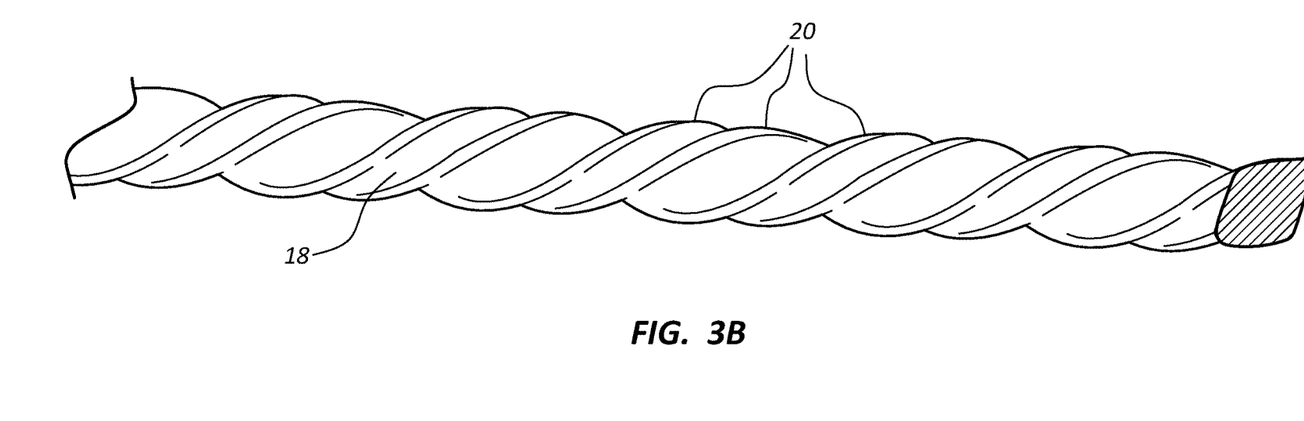
FIG. 3B also shows a close-up view of an exemplary section of a core in which ribs have been formed by rotating/twisting one portion of the core or core material relative to another portion thereof, but the embodiment in FIG. 3B has not been rotated/twisted as many times as shown in FIG. 3A so fewer ribs or more spaced-apart ribs are shown.

FIGS. 3A and 3B illustrate a portion of a ribbed core 18 in which the ribs have been formed on the core 18 or on a material used to form core 18 by twisting/rotating one portion or end of the core or material relative to another portion or end of the core or material. One portion or end of the core or material may be held in place or stationary while the other portion or end is twisted/rotated, or the portions or ends may be rotated at different speeds and/or in different directions. The rotation of one portion while holding another portion in place causes the core or material to twist and form the ribs 20. An initial preformed guidewire core material may be used in the method, or a new guidewire core material may be made for use in the method, e.g., by extrusion, mold, or other means. The initial preformed guidewire core material or newly formed core material may have a non-circular shape cross-section (e.g., a rectangular, square, pentagonal, hexagonal, other polygonal cross-section, or a cross-sectional shape similar to one of these but with rounded corners). The edges or corners of the shaped cross section may help to form the desired ribs 20. Any cross-sectional shape can be used but a square or roughly square cross-section, for example, allows equal right angles for gripping the rotated end prior to and during twisting/rotating and forms even ridges. One portion or end of the initial preformed guidewire core material or newly formed core material may be fixed in position while another portion or end is twisted/rotated, or both portions/ends may be rotated differently.

Different portions/regions of the core or guidewire core material may be twisted different amounts to form a varied outer surface, e.g., one region may have more turns per cm of length than another region, and one region may be coiled in one direction while another region is coiled in another direction. FIGS. 3A and 3B show portions/regions/guidewires that have been twisted/rotated different amounts. The twisting/rotating can plastically deform the core or guidewire core material. If necessary, after the desired coiled shape is obtained, the core 18 or material can be heat-treated or otherwise treated to make the deformation permanent. Also, edges and/or corners may be rounded to make them more atraumatic before or after rotation/twisting to form the coiled ribs. The number of coils per centimeter of length may vary, e.g., to allow for a wider or narrower coil shape and optimize the frictional characteristics.

The outer diameter of the core 18 and the guidewire 10 is determined by its use in the patient. In one embodiment, the core 18 and/or the overall guidewire 10 has an outer diameter of between 0.008 inches to 0.05 inches, between 0.01 inches to 0.04 inches, between 0.015 inches to 0.025 inches, or between 0.3 inches to 0.4 inches. By way of example, a core or guidewire outer diameter for urology uses may be within the range from 0.035 inches to 0.038 inches, while a vascular core or guidewire outer diameters may be within the range from 0.018 inches to 0.025 inches (e.g., within ±0.002 inches). Small core or guidewire outer diameters are possible for neurovascular uses, such as a range of 0.008 inches to 0.018 inches.

The core 18 may be formed from one or more of a variety of materials, including gold (radiopaque properties), nitinol (nickel-titanium alloy, which has exceptional shape-memory characteristics; may be used together with another material), platinum (radio-opaque properties), stainless steel, stainless steel with nickel, titanium, tungsten, fiberglass composites, carbon fiber, shape memory alloys, shape memory materials, and other suitable materials. In one embodiment, the core wire is a stainless steel core wire.

The core wire may include a reduced diameter region 26 as shown in FIG. 2 to provide added flexibility in the guidewire 10 in the portion of the guidewire corresponding to the reduced diameter region 26 of the core 18. The reduced diameter region 26 may be located at a distal end 12 to impart greater flexibility to the distal end 12 of the guidewire 10. Having a more flexible distal end 12 or distal region allows for improved navigability of the guidewire, e.g., it can make it easier to navigate the distal tip in the desired direction and/or into the desired pathway or vessel. Along the length of the reduced diameter region 26 from end to end, the reduced diameter region 26 may be entirely or partially tapered. The tapered region may be continuous or discontinuous. The grade of the taper may also change along the length of the reduced diameter region 26.

In FIG. 2, the reduced diameter region 26 of the core 18 is shown as including (in order from the ribbed portion of the core 18) a channel 22, a non-tapered region 40, and a tapered region 42 ending at a tip 24. The channel 22 facilitates secure connection of the core 18 to a cap 30. For example, the cap 30 may include a protrusion or lip that fits inside of the channel 22 (e.g., in a snap fit, a threaded fit, or other) to help secure the cap to the core 18. The channel 22 may be formed by adjacent ridges or ribs on the reduced diameter portion or may be a groove formed in an otherwise uniform outer surface area. The non-tapered region 40 may extend to the tip 24 or may terminate at any point along the length of the reduced diameter region 26. The tapered region 42 may extend from the channel 22 to the tip 24 or may extend over only a portion of the reduced diameter region 26. In one embodiment, the reduced diameter region 26 may be formed by grinding/machining a portion of the core wire 18 into the desired shape/configuration. Optionally, the core may include two reduced diameter regions on opposite ends of the core 18, each of which may have features/characteristics similar to those discussed above.

The tip 24 and reduced diameter region 26 may be covered by a cap 30 that fits over and around the reduced diameter region 26. If the core includes two reduced diameter regions on opposite ends, then both regions may be covered by a cap 30. The cap 30 may include a hollow center with both ends open or with one end closed. The cap 30 may be formed as a sleeve. The hollow center may be shaped to fit snuggly over the reduced diameter region 26 of the core 18. The cap 30 may be made of one or more than one of a variety of materials. In one embodiment, the cap 30 may be made of a polymer material, e.g., polyethylene, a combination of two or more of the foregoing materials, and/or other materials. In one embodiment, the cap 30 has an outer surface that is lubricious. In one embodiment, the material of the cap 30 itself is lubricious. In one embodiment, the cap 30 includes an outer coating that is lubricious. In one embodiment, the material of the cap 30 or a coating thereon is hydrophilic. There may also be some ribs (e.g., similar to ribs 20) on some or all of the outer surface of the cap 30. The cap 30 may have an outer diameter that is the same as or similar to (e.g., ±0.1 inches) the outer diameter of the remainder of the core (i.e., the region of the core not part of the reduced diameter region 26) to maintain a uniform or approximately uniform outer diameter of the guidewire 10 and have a smooth transition between the core 18 and the cap 30 along the length of the guidewire 10. Optionally, the cap 30 may have a uniform diameter or be tapered to a narrower diameter near its end, e.g., so the diameter at the edge of the cap facing the center of the guidewire is greater than the diameter at the opposite end or tip of the cap. The edge facing the center of the guidewire will generally have a diameter the same as or similar to the portion of the core it abuts to avoid an abrupt change in diameter from core to cap. The end or tip of the cap 30 may be blunt or atraumatic to avoid injury. A narrower diameter at the end or tip of the cap may help with navigation of the guidewire and/or entry into a new vessel or branch vessel.

The cap 30 may be designed to slide over the reduced diameter region 26 at the distal end 12 of the guidewire and the intermediate portion 14 of the guidewire to engage with a channel 22. The channel 22 may be configured as a snap-fit connection, and may engage the cap 30 with a portion of the cap 30 snapping into the channel 22. The snap-fit connection can be formed during manufacture, e.g., the cap may include a protrusion formed during a molding, 3D printing, etc. process to fit the channel 22. Snap-fit connections may be the simplest and most cost-effective way to assemble two parts, making them ideal for high-volume production because it is a quick and easy step to complete. This reduces the risk of improper assembly, which occurs more frequently during a step that requires more components and tools. However, other secure fastener connections are also possible, such as a threaded connection, an adhesive, chemical bonding, etc.

Figure 4:
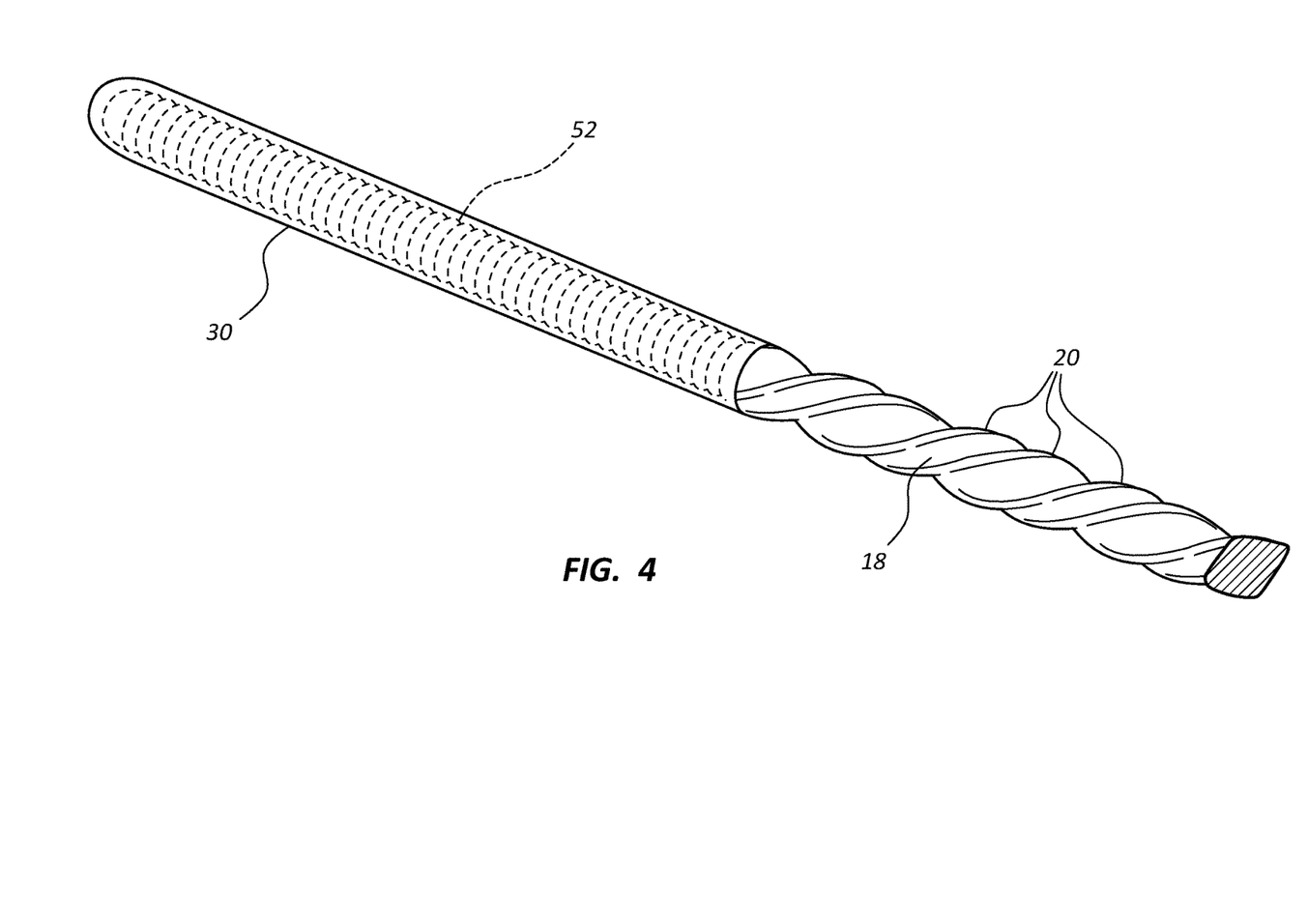
FIG. 4 shows a close-up view of a connection region between a core and a cap, the cap including an embedded coil therein.

The cap 30 may have lower surface friction or be more lubricious than the core 18 or the region of the core 18 including ribs 20. Lower surface friction of the cap 30 and thereby the distal end of the guidewire 10 helps the guidewire 10 navigate more smoothly through the desired pathway in the body and to the desired location and be more gentle on the patient, while greater surface friction of the ribbed region helps the guidewire retain its position and stay in the target location without undesired migration and allows the clinician to better grip and manipulate the guidewire 10. As discussed above, the reduced diameter region 26 of the core 18 allows the guidewire 10 to be flexible, less stiff, and the cap 30 preferably also facilitates greater flexibility in the distal region of the guidewire 10. The cap 30 may provide an atraumatic end and/or tip, thereby reducing the potential for injury as the guidewire is inserted into and navigated through a patient's body. The cap 30 may abut the ribs 20 or a region including ribs 20 and provide a smooth or relatively smooth transition between the core 18 and the cap 30, thereby avoiding an abrupt and drastic transition from ribbed or coiled region to the distal end. FIG. 4 shows a close-up view of a connection region between a core and a cap. Optionally, the cap 30 may be textured or may have a smooth surface for lower friction.

The cap 30 may be reinforced. For example, the cap 30 may include a support lattice, coil, wire, braid, or other support in a wall of the cap 30. In one embodiment, the cap 30 may be formed of a polymer material and a coil (e.g., a spring coil) is formed inside the polymer material. A spring coil can add strength to the cap while maintaining a high degree of flexibility. FIG. 4 shows a close-up view of a connection region between a core and a cap, the cap including an embedded coil 52 therein.

In one embodiment, the sleeve or cap 30 may be formed primarily or entirely as a spring coil over the reduced diameter region 26 of the guidewire 10. The spring coil may be designed to maintain the uniform or roughly uniform outer diameter and create a smooth transition from the ribbed region of the core 18. The outer diameter of the spring coil may be made to be the same as or similar to the outer diameter of the remainder of the core wire 18 (see discussion of outer diameter of the core wire 18 above).

The guidewire 10 may also include one or more coatings or outer layers 50 thereon for one or more of a variety of purposes. The coating(s) and/or layer(s) can be on the core 18, the cap 30, and/or both. The coating(s) and/or layer(s) can be applied by spray-coating, dip coating, other coating methods, and/or layering a material or more than one material over a portion of the guidewire. The guidewire 10 may be coated or layered with a plastic or polymer material, e.g., polytetrafluoroethylene (PTFE), expanded polytetrafluoroethylene (ePTFE), polyethylene, HDPE, LDPE, etc. Other coating(s) and/or layer(s) may be hydrophilic (lubricates for more gentle navigation and good trackability), anti-thrombogenic/heparin (inhibits clotting), hydrophobic (enhances tactile response for the clinician creating more responsive feel during surgical maneuvers), or silicone (reduces friction). Additionally, the outer surface of the guidewire 10, especially the distal region or the cap 30 may be coated or layered with a lubricious, hydrophilic, or hydrophobic coating to reduce friction. The coating(s) and/or layer(s) may extend over both the core and the cap and form a smooth, unbroken outer surface transition between the core and the cap.

Methods of medical treatment or methods of using a guidewire in a medical procedure may include obtaining a guidewire (e.g., the same as or similar to guidewire 10 discussed above) comprising a core (e.g., the same as or similar to core 18 discussed above) with preformed ribs (e.g., the same as or similar to ribs 20 discussed above). The preformed ribs may be along all or a portion (e.g., a proximal portion) of the core. The guidewire may also include a cap (e.g., the same as or similar to cap 30 discussed above). The cap may be positioned over a reduced diameter region of the core, e.g., at a distal end of the core. A distal end of the guidewire may be inserted into a patient's body lumen/vessel, and may be navigated to a desired target location in the patient's body. The guidewire may then be used to introduce a catheter or other device(s) along the guidewire to the target location inside the patient's body, e.g., the guidewire may be used to guide a catheter, scope, lead, or another medical device into a patient's vessels, such as a patient's urinary tract, vasculature, and/or other vessels. In urology/endourology medical procedures, the guidewire can be inserted into the urinary tract (e.g., through the urethra, bladder, into the ureter, and may also be moved up to or near the kidney). A catheter and/or ureteroscope may be advanced over the guidewire with the guidewire providing a path for the catheter and/or ureteroscope to traverse.

The above devices, components, systems, assemblies, methods, etc. have generally been described as being applied to guides and guidewires for medical treatment; however, the principles described may be applied to other types of devices, components, systems, assemblies, methods, etc. Further, the features described in one embodiment herein may generally be combined with features described in other embodiments herein. All of the devices, components, systems, assemblies, methods, etc. disclosed and claimed herein may be made and executed without undue experimentation in light of the present disclosure.

While the guides, guidewires, devices, components, systems, assemblies, methods, etc. of this invention may have been described in terms of particular variations and illustrative figures, it will be apparent to those skilled in the art that the invention is not so limited and that variations may be applied to the guides, guidewires, devices, components, systems, assemblies, methods, etc. For example, with respect to the methods, uses, and/or steps described herein variations may occur in the steps, uses, the sequence/order of steps, etc. described herein without departing from the concept, spirit, and scope of the invention, as defined by the claims. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

The invention claimed is:

1. A guidewire, comprising:
   a cap; and
   a core, comprising:
      one or more ribs formed along a first portion of the core, the first portion of the core having a first diameter, wherein the one or more ribs increase the friction of an outer surface of the guidewire; and
      a reduced diameter region distal of the first portion having a second diameter less than the first diameter, the reduced diameter region including a channel adjacent to the first portion, wherein the channel is shaped to mate with a portion of the cap in a snap-fit or threaded connection.

2. The guidewire according to claim 1, wherein the cap has a same or a similar diameter to the first diameter, the cap positioned over the reduced diameter region of the core such that an edge of the cap abuts the first portion.

3. The guidewire according to claim 2, further comprising a coating on the first portion of the core.

4. The guidewire according to claim 3, wherein the coating extends over the cap and forms a smooth, unbroken outer surface transition between the first portion of the core and the cap.

5. The guidewire according to claim 1, wherein the cap has a smooth, uniform outer surface.

6. The guidewire according to claim 1, wherein the one or more ribs are arranged as one or more helical coils along the first portion.

* * * * *